(12) United States Patent
Akui et al.

(10) Patent No.: US 8,953,031 B2
(45) Date of Patent: Feb. 10, 2015

(54) MEDICAL DEVICE WHICH ACQUIRES THE PICTURE FOR OBSERVATION

(71) Applicant: Olympus Medical Systems Corp., Tokyo (JP)

(72) Inventors: Nobuaki Akui, Hino (JP); Satoshi Takekoshi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 17 days.

(21) Appl. No.: 13/785,722

(22) Filed: Mar. 5, 2013

(65) Prior Publication Data

US 2013/0258081 A1    Oct. 3, 2013

Related U.S. Application Data

(63) Continuation of application No. PCT/JP2012/066001, filed on Jun. 22, 2012.

(30) Foreign Application Priority Data

Aug. 10, 2011    (JP) .................................. 2011-175163

(51) Int. Cl.
*A61B 1/04* (2006.01)
*A61B 1/06* (2006.01)
*H04N 9/47* (2006.01)
(Continued)

(52) U.S. Cl.
CPC ............ *G02B 23/24* (2013.01); *A61B 1/00183* (2013.01); *A61B 1/0607* (2013.01); *G02B 23/2423* (2013.01); *G02B 23/2461* (2013.01)
USPC .......................................................... 348/68

(58) Field of Classification Search
CPC ................... H04N 2005/2255; H04N 5/2354; H04N 5/2256; A61B 1/05; A61B 1/06; A61B 1/042; A61B 1/0669; A61B 1/045; G06T 2207/10068; G06T 2207/10152
USPC .......................................................... 348/68
See application file for complete search history.

(56) References Cited

U.S. PATENT DOCUMENTS

| 4,697,577 A | 10/1987 | Forkner |
| 2003/0216617 A1* | 11/2003 | Hirakui et al. ................. 600/159 |

FOREIGN PATENT DOCUMENTS

| GB | 1 262 214 | 2/1972 |
| JP | A-52-071888 | 6/1977 |

(Continued)

OTHER PUBLICATIONS

Office Action issued in Japanese Application No. 2013-510377 dated Apr. 16, 2013 (with translation).

(Continued)

*Primary Examiner* — Andy Rao
*Assistant Examiner* — Jared Walker
(74) *Attorney, Agent, or Firm* — Oliff PLC

(57) ABSTRACT

In a medical device, a field-of-view switching mechanism which moves a field of view imaged by an observation section, and an illumination-light switching mechanism including an illumination section having an illumination range of illumination light whose entire field of view is covered by movement, are configured integrally with each other. The illumination light is illuminated to the current field of view by moving the illumination range of the illumination light, in synchronism with pivoting of an observation and in compliance with the field of view.

18 Claims, 15 Drawing Sheets

(51) Int. Cl.
*G02B 23/24* (2006.01)
*A61B 1/00* (2006.01)

(56) References Cited

FOREIGN PATENT DOCUMENTS

| JP | A-62-284626 | 12/1987 |
| JP | A-2001-161630 | 6/2001 |
| JP | A-2004-147777 | 5/2004 |
| JP | A-2005-334275 | 12/2005 |
| WO | WO 2010/014421 A1 | 2/2010 |

OTHER PUBLICATIONS

Feb. 20, 2014 International Preliminary Report on Patentability issued in PCT Application No. PCT/JP2012/066001.
International Search Report issued in International Application No. PCT/JP2012/066001 dated Sep. 18, 2012 (with translation).

* cited by examiner

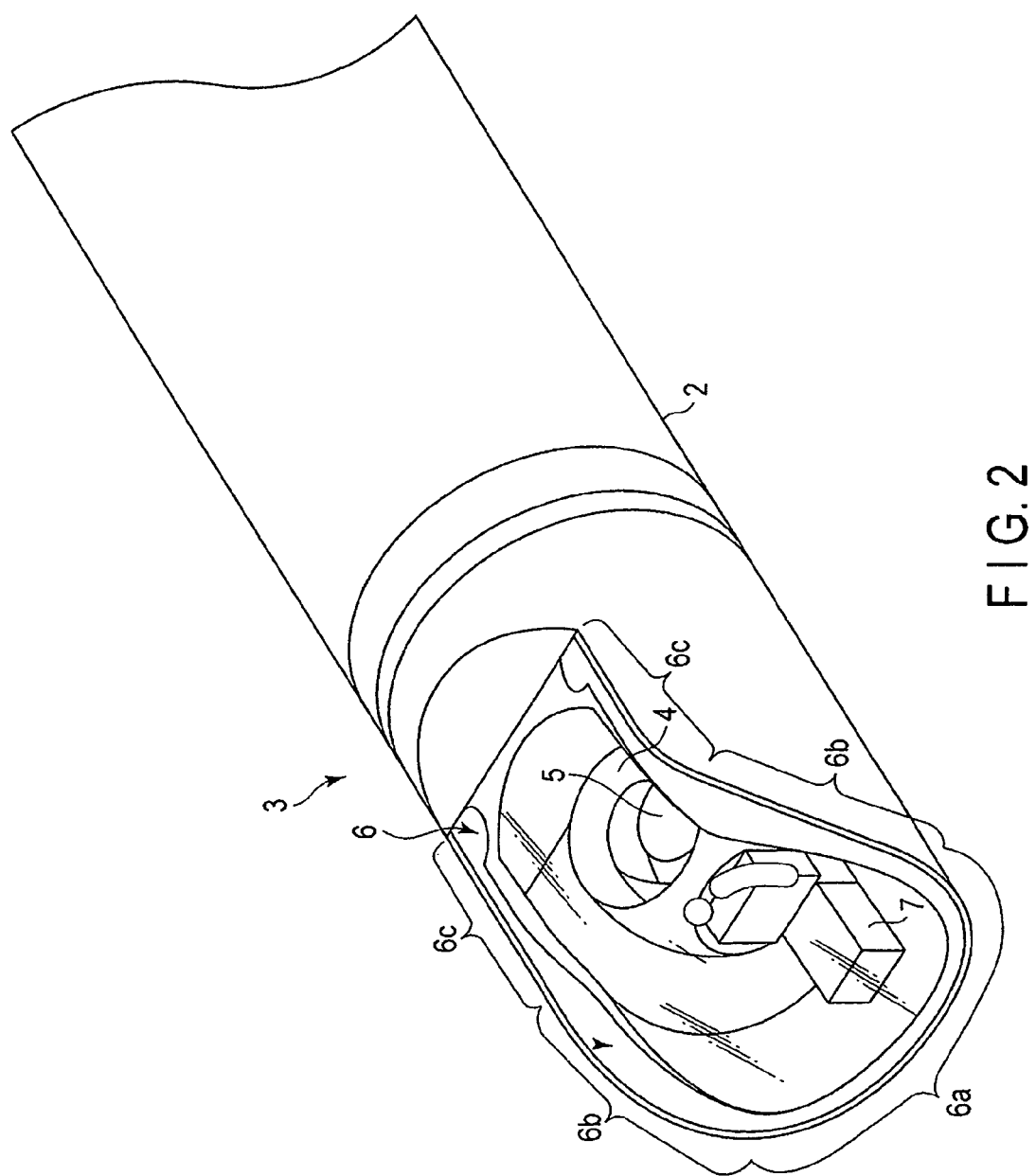
F I G. 2

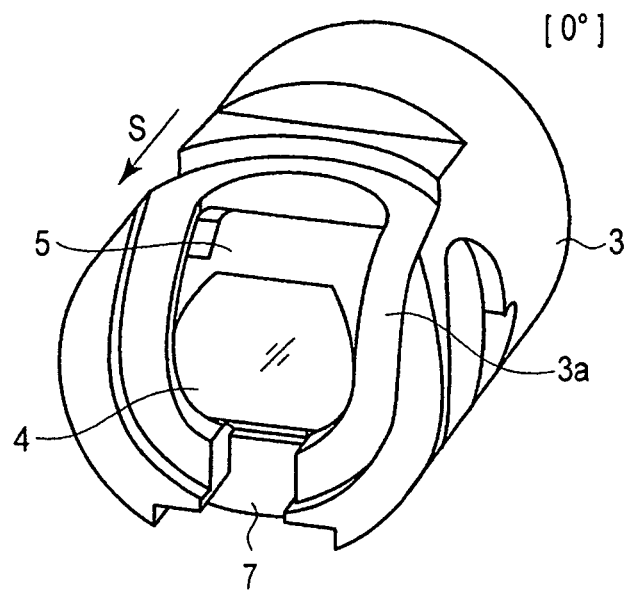
F I G. 4A
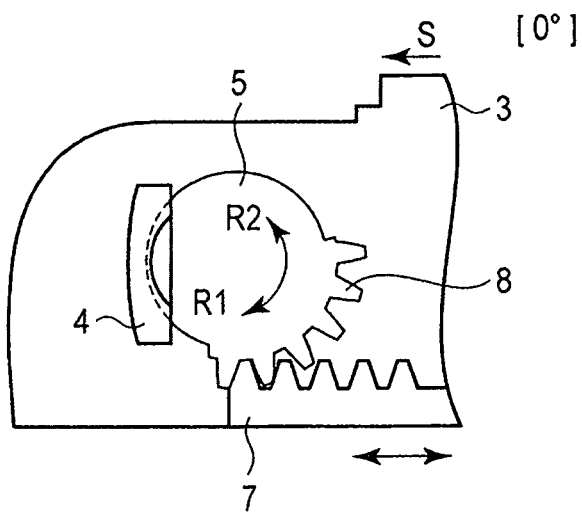
F I G. 4B

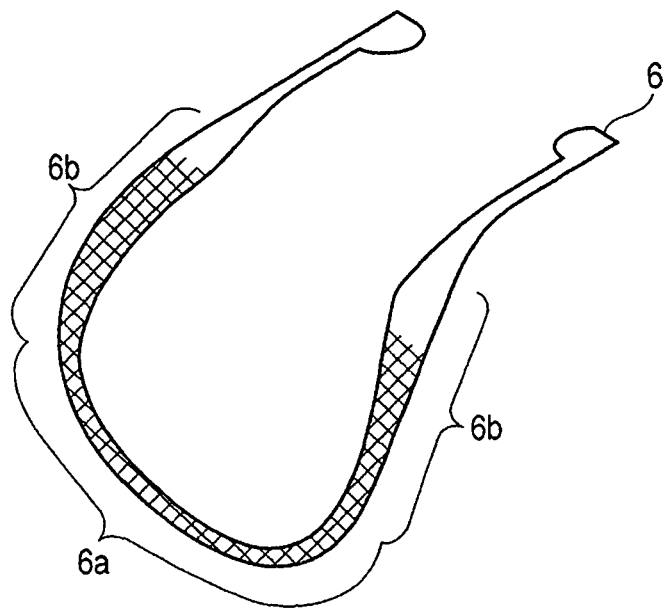
F I G. 4C
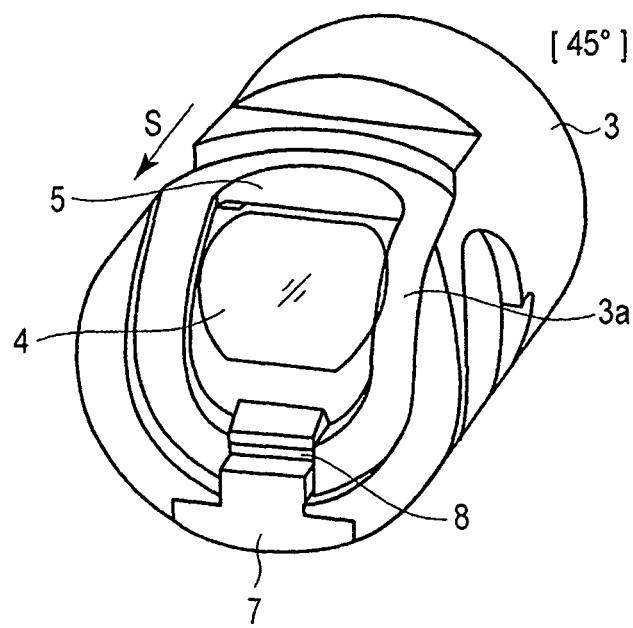
F I G. 5A

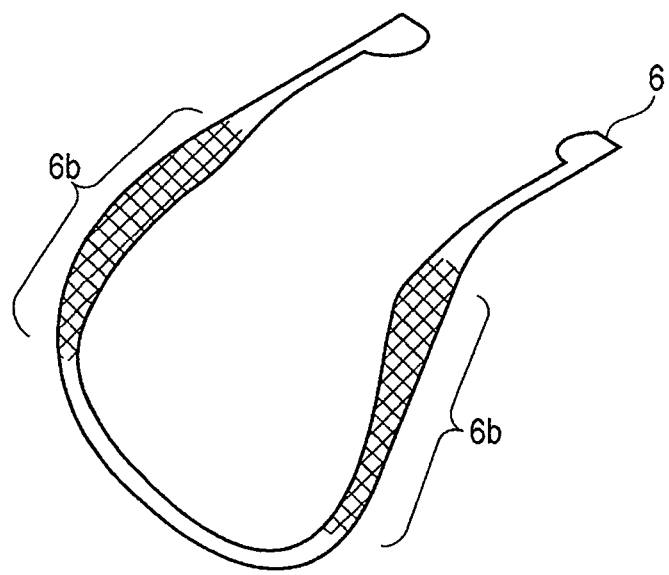
F I G. 5B
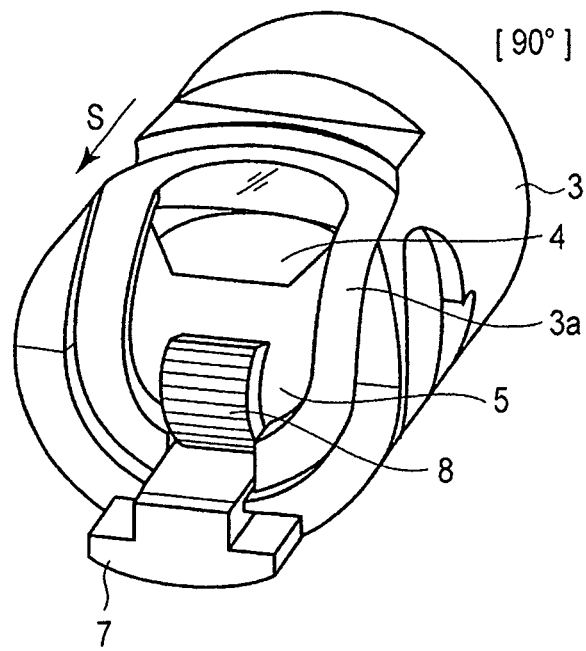
F I G. 6A

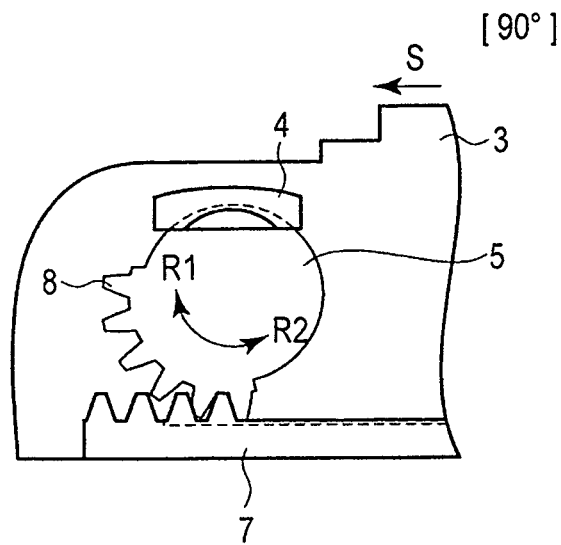
F I G. 6B
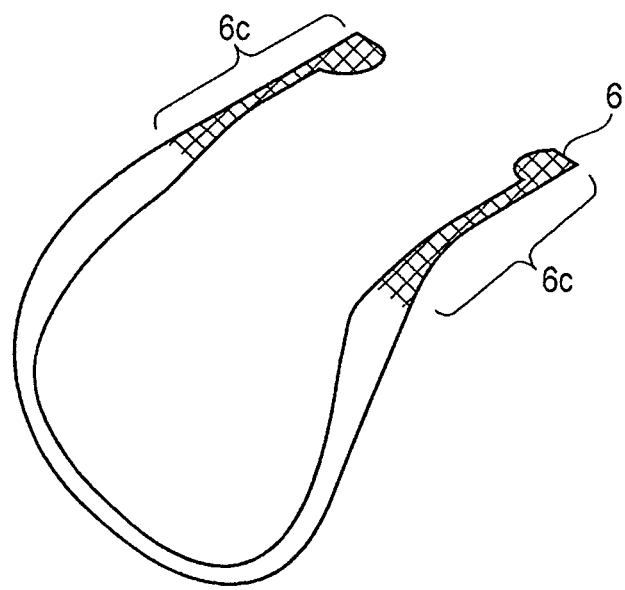
F I G. 6C

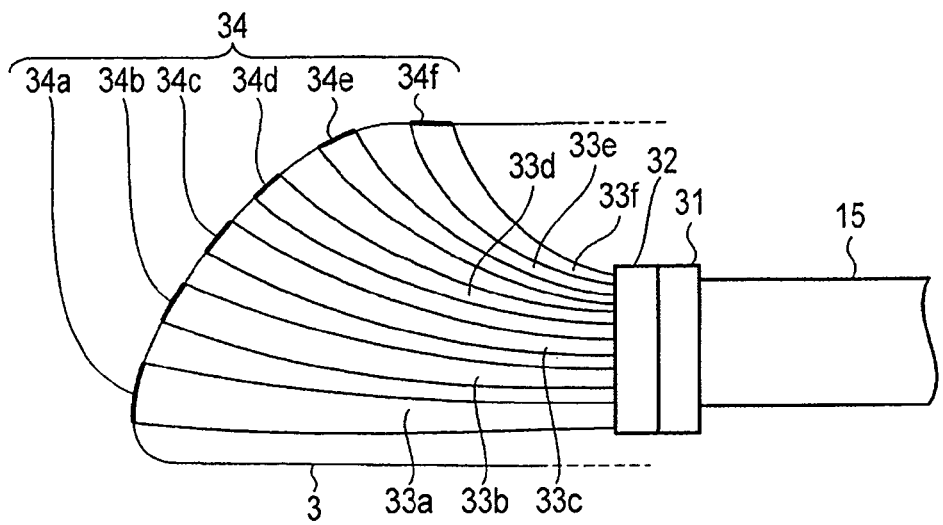
F I G. 13A
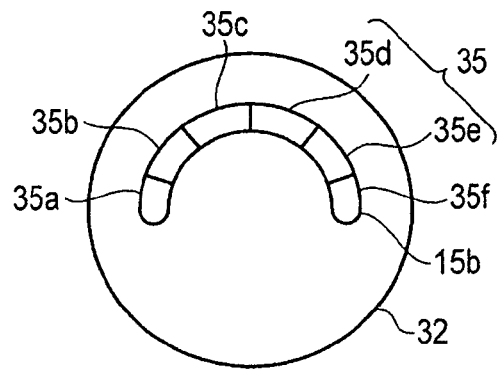
F I G. 13B
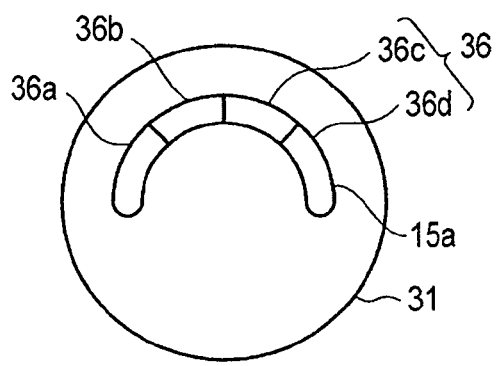
F I G. 13C

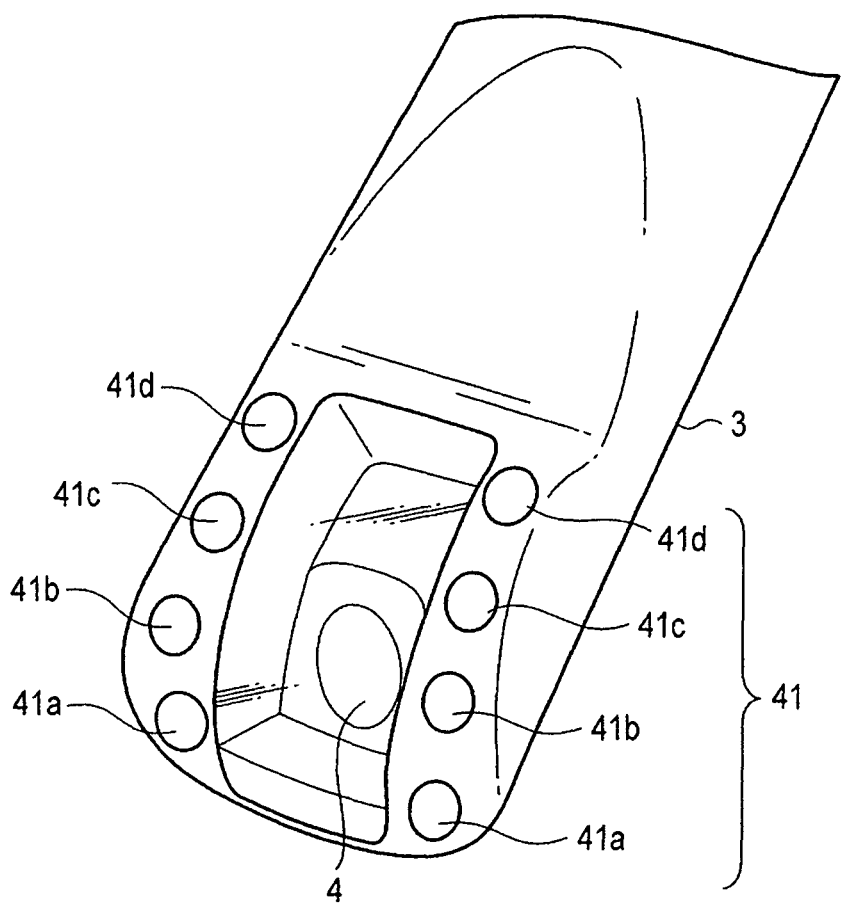
F I G. 14

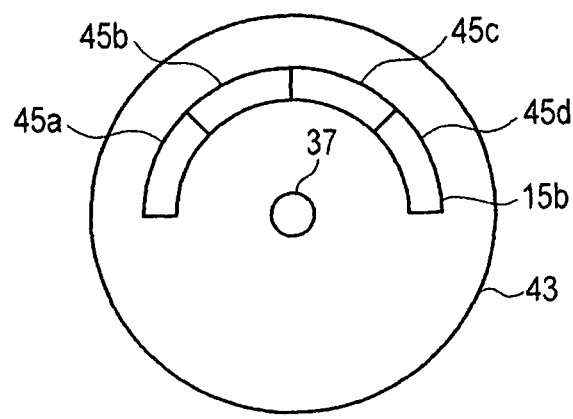
F I G. 15A
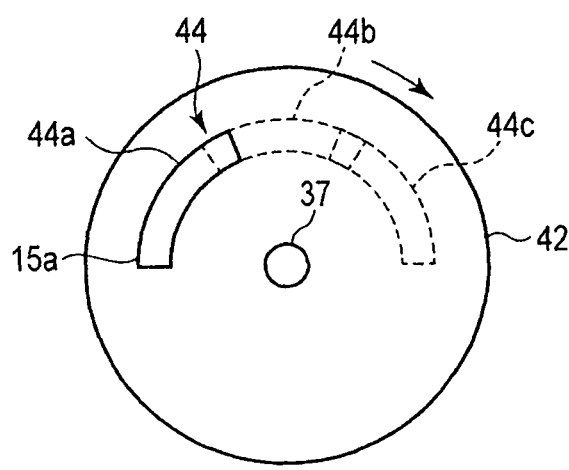
F I G. 15B

MEDICAL DEVICE WHICH ACQUIRES THE PICTURE FOR OBSERVATION

CROSS-REFERENCE TO RELATED APPLICATIONS

This is a Continuation Application of PCT Application No. PCT/JP2012/066001, filed Jun. 22, 2012, which was published under PCT Article 21(2) in Japanese.

This application is based upon and claims the benefit of priority from prior the Japanese Patent Application No. 2011-175163, filed Aug. 10, 2011 the entire contents of which are incorporated here by references.

BACKGROUND OF THE INVENTION

1. Field of the Invention

The invention relates to a medical device which illuminates in accordance with moving of a field of view, and obtains image information of an object to observe.

2. Description of the Related Art

At a tip end of a body of an endoscope as a medical devicemedical device, there are provided an imaging apparatus which obtains a video image as image information by imaging an object to observe, and an illumination unit which illuminates the object for imaging. The imaging apparatus does not need movement of the field of view to image and employs an imaging optical system with a fixed focus up to the present. The field of view is therefore fixed. A common illumination unit is provided with an illumination window at a tip end thereof, and guides illumination light with a light guide fiber from an external light source, in order that an area slightly greater than a field of view is illuminated at a desired uniform luminous intensity.

In a rigid endoscope, an insertion unit is hard, and an imaging apparatus (objective lens) provided at a tip end thereof is integrated with the insertion unit. Therefore, the insertion unit needs to be moved in order to catch a portion to observe within a field of view.

In contrast, as a technology to move a field of view without moving an insertion unit, for example, Jap. Pat. Appln. KOKAI Publication No. 52-71888 proposes an endoscope of a field-of-view transformable type in which a pivotal field-of-view transformer is provided at a tip end of an image guide. In brief, a mirror is provided to be pivotal. The field-of-view transformer is connected to a wire, and the field of view is observed arbitrarily by pushing and pulling the wire.

Jpn. Pat. Appln. KOKAI Publication. No. 52-71888 proposes a conceptual embodiment. When applied to an endoscope in which a solid-state image sensing device, such as a CCD, is used as an imaging apparatus, a movement mechanism which makes the imaging apparatus movable together with an illumination unit has a complex configuration, and a tip end is not easy to make smaller.

Accordingly, even in a mechanism which makes an imaging apparatus movable, an illumination window for emitting illumination light is fixed to a tip end. The mechanism can easily have a configuration for illumination which covers a whole range of a field of view of the movable imaging apparatus. In a proposed endoscope which makes an imaging apparatus movable, illumination is constantly achieved so as to cover a whole field of view within a movable range of the imaging apparatus from an illumination window.

BRIEF SUMMARY OF THE INVENTION

An embodiment according to the invention relates to a medical instrument mounting an imaging apparatus which moves a field of view, includes an illumination apparatus which selectively illuminates a range of a field of view, suppresses energy consumed by illumination, and achieves downsizing of an insertion unit.

Further, an embodiment according to the invention relates to a medical device comprising: an observation section capable of moving a field of view within a predetermined range; a field-of-view switching mechanism that moves the field of view by pivoting the observation section in accordance with a movement operation by an operation portion; an illumination section that illuminates illumination light guided from outside of the operation portion, toward a field of view within the range through an illumination port; an illumination-light switching mechanism provided inside the operation portion and comprising a light inlet surface that guides the illumination light to the illumination port, and a light outlet surface that is opposed to the light inlet surface and emits the illumination light to the light inlet surface, wherein the light outlet surface moves in relation to the light inlet surface, in accordance with the movement operation by the operating portion, and selectively guides the illumination light to a part of the illumination port; and a synchronous section provided inside the operation portion and comprising a mechanism that makes the illumination light-switching mechanism selectively emit the illumination light to a light inlet surface for emitting the illumination light in a direction including the range of the field of view, in synchronism with operation of the field-of-view switching mechanism that moves the observation section to the range of the field of view.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a perspective view showing an exterior configuration of a tip end mechanism of an insertion section of a body of an endoscope apparatus;

FIG. 4A shows a state of an imaging section where a field of view is directed in a direction of 0 degree;

FIG. 4B shows a positional relationship between the imaging section and a rack section;

FIG. 4C shows an area of an illumination port which emits illumination light when the field of view is directed in the direction of 0 degree;

FIG. 5A shows a state of the imaging section where the field of view is directed in a direction of 45 degrees;

FIG. 5B shows an area of the illumination port which emits illumination light when the field of view is directed in the direction of 45 degrees;

FIG. 6A shows a state of the imaging section where the field of view is directed in a direction of 90 degrees;

FIG. 6B shows a positional relationship between the imaging section and the rack section;

FIG. 6C shows an area of the illumination port which emits illumination light when the field of view is directed in the direction of 90 degrees;

FIG. 13A conceptually shows an example configuration of an illumination-light switching mechanism provided at a tip end of an insertion section of a rigid endoscope according to the second embodiment;

FIG. 13B shows a light inlet surface on the side of the insertion section;

FIG. 13C shows a light outlet surface having a liquid crystal shutter;

FIG. 14 shows an exterior configuration of an illumination-light switching mechanism provided at a tip end of an insertion section of a rigid endoscope according to the third embodiment;

FIG. 15A shows a light inlet surface on the side of an insertion section; and

FIG. 15B shows a light outlet surface having a mechanical shutter plate.

DETAILED DESCRIPTION OF THE INVENTION

Hereinafter, embodiments of the invention will be described in details with reference to the drawings.

First Embodiment

Figure 1A:
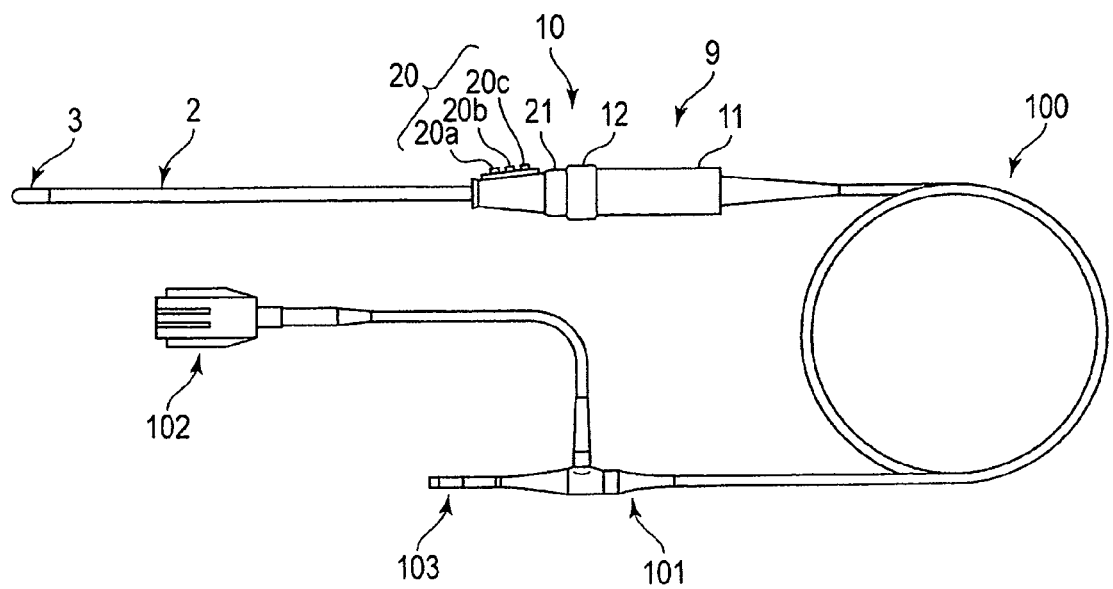
FIG. 1A shows an exterior configuration of an endoscope apparatus as an embodiment according to a medical device-medical device of the invention.
Figure 1B:
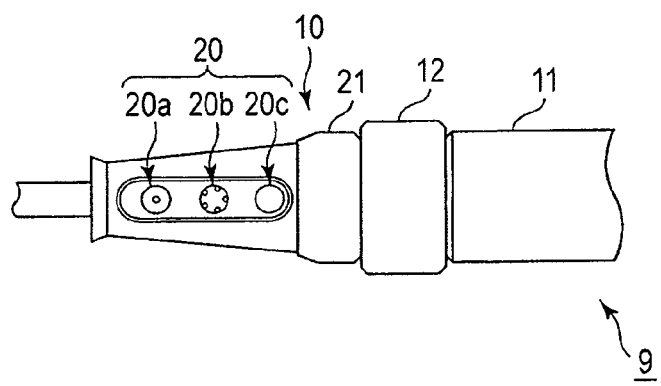
FIG. 1B shows an exterior configuration of an operation unit 9 of the endoscope apparatus.

FIG. 1A shows an exterior configuration of an endoscope apparatus as an embodiment according to a medical device of the invention. FIG. 1B shows an exterior configuration of an operation section 9 of the endoscope apparatus.

FIG. 2 is a perspective view showing an exterior configuration of a tip end mechanism of an insertion section in a body of an endoscope apparatus.

The present embodiment describes, as an example, the configuration of a tip end provided on a rigid insertion section in a rigid endoscope. The illumination section of the present embodiment has an illumination range of illumination light which covers a whole field of view (or the all field of view to image) to observe, and illuminates a partial illumination area with illumination light, targeting a current field of view, in synchronism with pivoting of an observation section (or an imaging section). In each of embodiments and modifications described below, the observation section will be described as an imaging section including an image sensor which obtains image data (a video signal). However, when an image need not be obtained but only visual observation is needed, the observation section may be configured by a lens optical system. The observation section includes an imaging section, and a visually viewable range or an image-sensible range in the observation section or the imaging section each are referred to as field of view.

An endoscope apparatus 1 is configured by: an insertion section 2 which is inserted into a body cavity; a tip-end mechanism section 3 provided at a tip end of the insertion section 2; an operation section 9 including a field-of-view switching mechanism 10 which is provided on the base-end side of the insertion section 2 and changes a field of view by pivoting an imaging section described later, and an illumination-light switching mechanism (partially included in the field-of-view switching mechanism) which selects/switches illumination light; a universal cable 100 including a light guide fiber (or a optical fiber cable) 15 as a light guide path which propagates illumination light and a signal cable; a camera plug 102 for connection with an unillustrated camera; a light guide connector 101 for optically branching from the universal cable 100 to the camera plug 102; and a light guide adapter 103 for connection with an unillustrated light source apparatus which generates light of a predetermined variable wavelength range and a system controller (such as a CCU). The operation section 9 is provided with three remote control switches 20 (20a, 20b, 20c) used for imaging, etc. The illumination section is configured by a light source apparatus, a light guide fiber 15, and an illumination port 6 (or a light-guide emission end).

The tip-end mechanism section 3 is on the tip-end side of the insertion section 2, and as shown in FIG. 2, is provided with the imaging section 5 which moves a field of view by pivoting, and an illumination port 6 of the illumination section, which illuminates illumination light capable of covering the whole field of view of a movable range. On a tip-end face of the tip-end mechanism section 3 shown in FIG. 2, an unillustrated transparent cover lens is provided along an inner side of the illumination port 6 in a manner that the imaging section 5 and the inside where the objective lens 4 is provided are kept watertight. Of course, the transparent cover lens may be provided so as to cover upside of the illumination port included. The imaging section 5 is pivoted by a rack-and-pinion mechanism (a rack section 7, a gear (pinion) section 8) described later, and integrally pivots the objective lens 4.

Pivoting of the imaging section 5 provided in the tip-end mechanism section 3 will now described.

FIG. 4A shows a state of the imaging section in which the field of view of the field-of-view switching mechanism 10 with an external cover detached is directed in the direction of 0 degree. FIG. 4B shows a positional relationship of the imaging section and the rack section.

As shown in FIG. 4B, the imaging section 5 is stored in a frame 3a, for example, pivotally supported in a manner that a housing is formed in a shape like a drum and is laid down sideways. The objective lens 4 is provided on a side face of the drum of the housing, and an imaging unit (unillustrated) is contained inside. The imaging unit comprises a solid-state image sensor (CCD) which receives an optical image converged and focused by the objective lens 4, performs an image processing on a video signal, generates image information (image data), and sends the image information to a camera control unit (CCU).

The gear section 8 is provided on a lower surface of the housing of the imaging section 5. The rack section 7 in which a gear to be engaged with the gear section 8 is formed is provided to be movable. The rack section 7 is moved back and forth by the field-of-view switching mechanism 10 described later, which is provided in the operation section 9. In accordance with the back and forth movement, the engaged imaging section 5 is pivoted, and the objective lens 4 is pivoted, for example, from 0 degree (horizontal direction: axial direction in which the insertion section 2 advances) shown in FIG. 4B to at least 90 degrees shown in FIG. 6B described later. Insofar as the illumination light falls within a range, the range is not limited to 0 to 90 degrees.

Although the present embodiment is configured to mount the imaging unit in the imaging section 5 and to pivot the imaging section 5, the present embodiment is not limited to the configuration. Alternatively, the configuration may be arranged to pivot only the optical system by separating an imaging unit which includes an image sensor and generates a video signal, from the optical system which forms an optical image of an object to observe. That is, in the optical system, a pivotal section may be configured by an objective lens and a light guide section, such as a prism, which refracts and guides light flux forming an image (an optical image) to an imaging unit.

Also, the present embodiment employs a rolling mechanism which combines the rack section 7 and the gear section 8. The present embodiment is not limited to this mechanism but may be configured in a manner that a pulley is attached to a support shaft which pivotally supports the imaging section 5 by combining the pulley and a wire and another pulley is also attached to a motor shaft. A wire may be stretched therebetween and the imaging section may be pivoted by pulling the wire. At this time, a member which applies an energizing force, such as a flat spiral spring, may be attached to the pulley engaged in the support shaft so as to allow the rotated pulley to return to an arbitrarily determined reference position.

An end face (light illumination surface) of the unillustrated light guide fibers are arranged at the illumination port 6 from the back side. The number of fiber end face is arranged at the illumination port 6 at a uniform distribution in this case. However, positioning of the fiber end face is not limited to a uniform distribution. The fiber end face may be dense to increase an amount of light illuminated in the horizontal direction (0 degree). The fiber end face may be arranged to be sparse to decrease an amount of light illuminated in the upward direction. A rate of an amount of light to illuminate may be changed depending on design. Otherwise, if the fiber end face is arranged to be different from the sparse and dense arrangements, the different arrangement may be achieved by changing the width of the illumination port 6 at a uniform density.

Next, the field-of-view switching mechanism 10 will be described.

Figure 3:
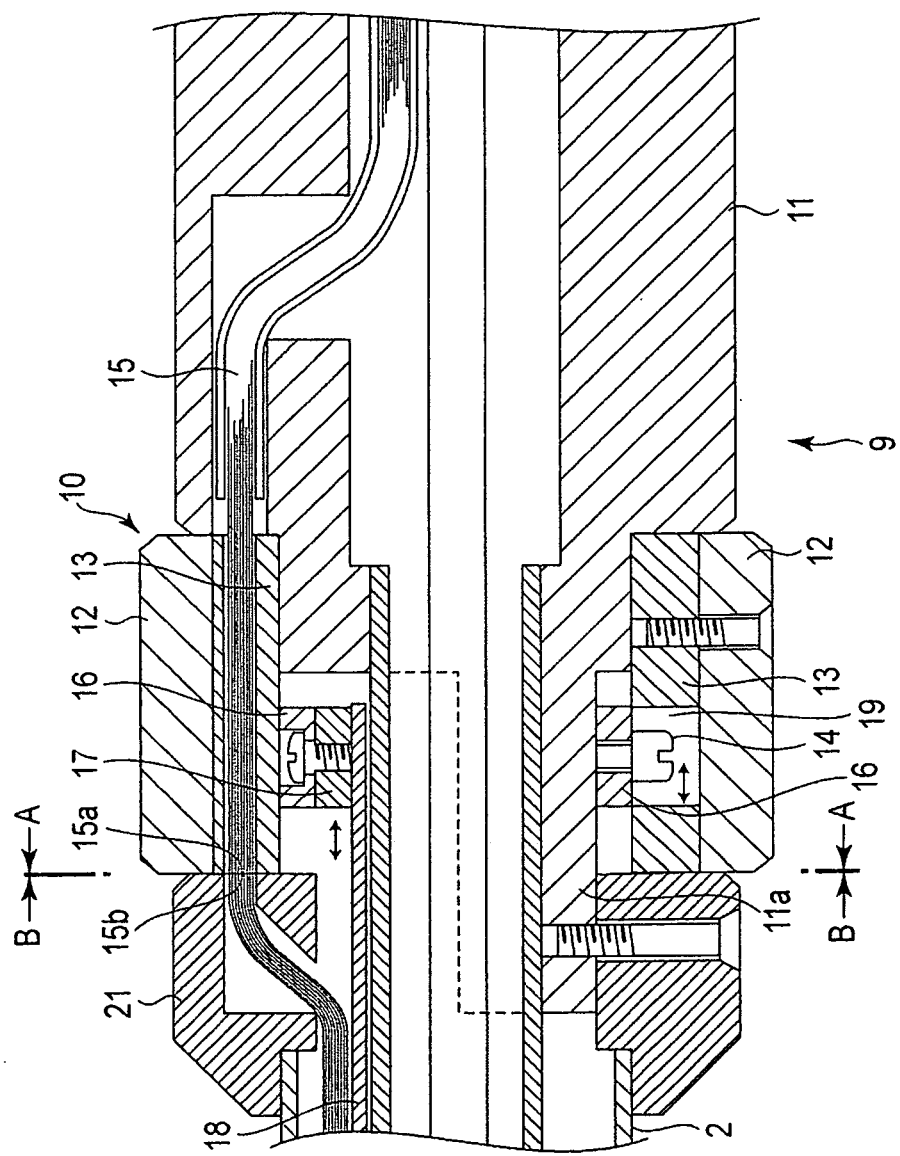
FIG. 3 shows a cross-sectional configuration of a field-of-view switching mechanism according to the first embodiment.

FIG. 3 shows a cross-sectional configuration of the field-of-view switching mechanism according to the first embodiment.

The field-of-view switching mechanism 10 is provided in the operation section 9. The field-of-view switching mechanism 10 is configured integrally by a mechanism which pivots the objective lens 4 by pivoting the imaging section 5, to change a direction of a field of view, and a mechanism which selects/switches an illumination area (partial illumination areas 6a, 6b, and 6c) of the illumination light through the illumination port 6, depending on the current field of view.

As shown in FIG. 3, a grip 11 of the operation section 9 and the insertion section 2 are connected. Specifically, an operation half-pipe 18 on the side of the insertion section 2 is engaged on a fixed pipe 11a of the grip 11 which contains a signal cable in a manner that the operation half-pipe 18 is movable back and forth. The operation half-pipe 18 is connected to an end of the aforementioned rack section 7 directly or through a wire, etc.

The field-of-view switching mechanism which moves the field of view is configured mainly by the grip 11, a rotary ring 12 as an operation section, the cam 13 (emitting light-guide cap), a cam pin 14, a movable ring 16, the operation half-pipe 18, the rack section 7, and the gear section 8. In this configuration, the signal cable is wired at the center part of the grip 11, and the fixed pipe 11a penetrating to a tip-end mechanism section 3 is provided. An end of the fixed pipe 11a is cut out by half and stepped, as shown in FIG. 8B, exposing the fixed pipe 11a throughout the half of the circumference thereof.

The operation half-pipe 18 is engaged on the cutout part of the fixed pipe 11a in a manner that the operation half-pipe 18 is opposed to and corresponds to the cutout part. As the semicircle of the operation half-pipe 18 makes contact with the cutout part, the operation half-pipe 18 is restricted from rotating and is allowed to move back and forth.

Figure 8A:
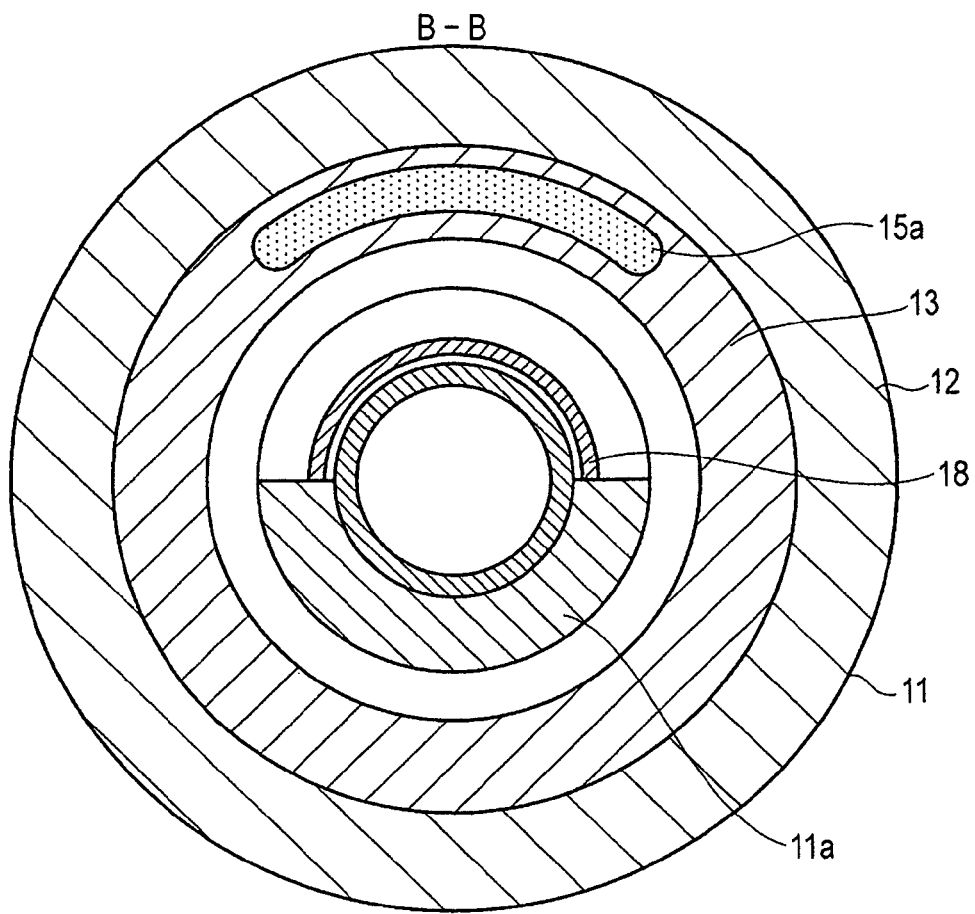
FIG. 8A shows a cross-sectional configuration of the illumination-light switching mechanism on the side of a universal cable, viewed from the B-B side of FIG. 3.
Figure 8B:
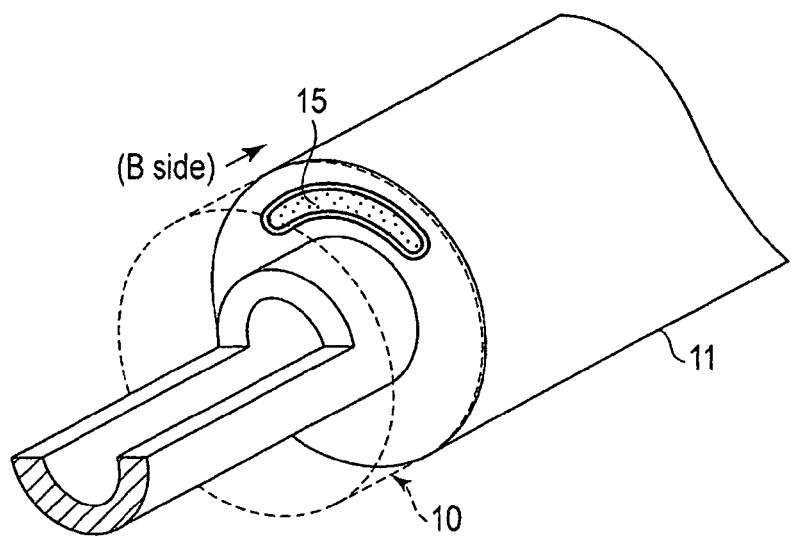
FIG. 8B shows a schematic configuration of the illumination-light switching mechanism viewed in an oblique direction from the B-B side.

In the cam 13, as shown in FIG. 8A, a light guide fiber (light guide path) 15 which guides light flux from a light source is provided semicircular, sharp forming a flat light outlet surface 15a made of the fiber end faces. The cam 13 is fixed by the rotary ring 12 and by screwing. As the rotary ring 12 is rotated, the rotary ring 12 rotates on the grip. As shown in FIG. 3, a semi-cylindrical member 17 is fixed to an outer surface of the operation half-pipe 18. The movable ring 16 is fixed to the semi-cylindrical member 17 by screwing.

The movable ring 16 and the cam 13 are configured so as to move and slide relatively to each other with a slight gap maintained therebetween as the movable ring 16 moves back and forth and the cam 13 moves in a rotating direction. The outer half-circumferential surfaces of the movable ring 16 and the grip 11 which make contact with the inner circumferential surface of the cam 13 may be made of, for example, hard-resin-made members as a material or metal members subjected to a surface processing, in order to reduce contact friction. Alternatively, bearings may be used.

Figure 11A:
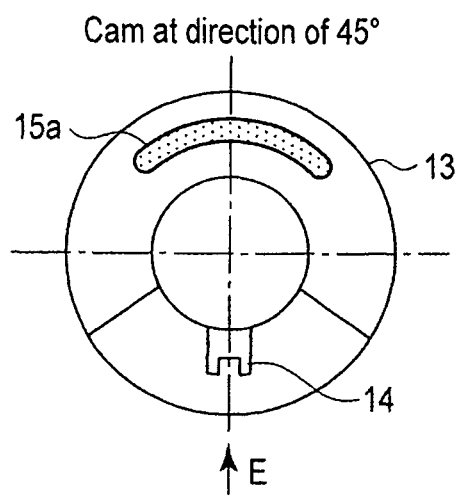
FIG. 11A shows a position of the light outlet surface where the field of view of the imaging section is directed in the direction of 45 degrees.
Figure 11B:
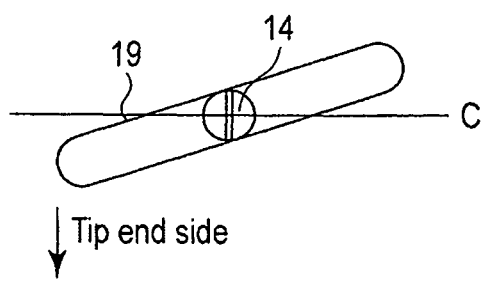
FIG. 11B shows a position of the cam pin in the guide hole corresponding to the position of the light outlet surface.

The cam pin 14 is fixed by screwing to the movable ring 16, and a head section of the cam pin 14 is slidably engaged in a guide hole 19 formed in an oblique direction in the cam 13 as shown in FIG. 11B. The head section of the cam pin 14 shown in FIG. 3 is shown to maintain a gap from a wall surface of the guide hole 19. This gap appears since an oblique groove is cut in a horizontal direction C. In actual, however, only a gap which is needed for sliding is provided.

In this configuration, the movable ring 16 to which the cam pin 14 is fixed is fixed to the operation half-pipe 18 through the semi-cylindrical member 17. Since the operation half-pipe 18 is in contact with a part of the cutout part of the fixed pipe 11a, as described above, the operation half-pipe 18 is movable only in rotation-axis directions perpendicular to rotation directions, i.e., back and forth directions. That is, the cam pin 14 is movable only in longitudinal directions (back and forth directions) of the guide hole 19 extending obliquely.

Figure 7:
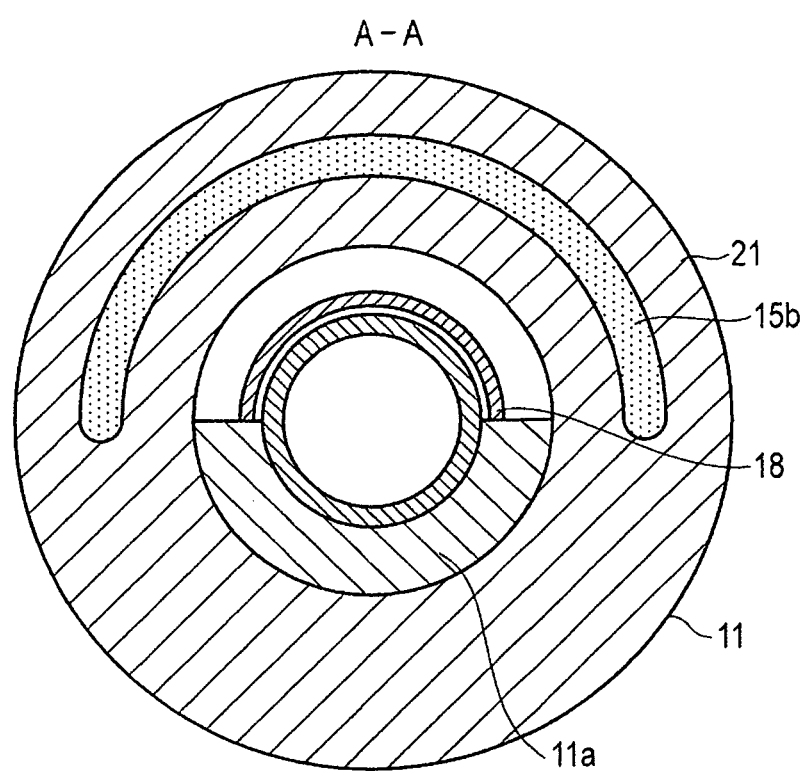
FIG. 7 shows a cross-sectional configuration of an illumination-light switching mechanism on the side of the insertion section, viewed from the A-A side of FIG. 3.

Accordingly, as the rotary ring 12 is pivoted, the cam 13 is integrally pivoted together. The guide hole 19 of the cam 13 is also pivoted, and the engaged cam pin 14 is pushed and pulled in the back and forth directions by a force in a pivoting direction of the guide hole 19. Therefore, the operation half-pipe 18 moves back and forth the rack section 7 by back and forth movement of the cam pin 14, thereby pivoting the imaging section 5. A pivotal range of the rotary ring 12 is within a range (angles) throughout which the light outlet surface 15a moves in the light inlet surface 15b shown in FIG. 7.

With reference to FIGS. 4A, 4B, 4C, 5A, 5B, 6A, 6B, and 6C, a description will be made of changing of the field of view at the imaging section 5.

FIG. 4C shows partial illumination areas (hatched parts) of the illumination port which emits illumination light when the field of view is directed in the direction of 0 degree. FIG. 5A shows a state of the imaging section when the field of view of the field-of-view switching mechanism 10 is directed in the direction of 45 degrees. FIG. 5B shows partial illumination areas (hatched parts) of the illumination port which emits illumination light when the field of view is directed in the direction of 45 degrees. FIG. 6A shows a state of the imaging section when the field of view of the field-of-view switching mechanism 10 is directed in the direction of 90 degrees. FIG. 6B shows a positional relationship between the imaging section and the rack section. FIG. 6C shows partial illumination areas (hatched parts) of the illumination port which emits illumination light when the field of view is directed in the direction of 90 degrees. In the present embodiment, the illumination range of the illumination light which is illuminated from partial illumination areas (for example, 6a, 6b, and 6c) is an approximate range not smaller than a field-of-view range, and at least inside of the field of view is uniformly illuminated at an equal luminous intensity.

As shown in FIG. 4A, when the optical axis of the objective lens is coaxial with an insertion direction s, the field of view (for example, the center of the field-of-view range) is set to 0 degree. At this time, as shown in FIG. 4C, illumination light is illuminated to the range of the field-of-view in the direction at 0 degree from the illumination area 6a of the illumination port 6. As shown in FIG. 4B, the rack section 7 engages with the pinion section 8 of the imaging section 5 when the rack section 7 is most retracted back. As an operator rotates the rotary ring 12 as described above, the operation half-pipe 18 moves forth, and accordingly, the rack section 7 also moves forth. As shown in FIG. 5A, forth movement of the rack section 7 causes the engaged imaging section 5 to pivot, and the field of view moves to 45 degrees. At this time, as shown in FIG. 5B, illumination light is illuminated to the field-of-view range in the direction at 45 degrees from the illumination area 6b of the illumination port 6.

Further, forth movement of the rack section 7 causes the imaging section 5 to pivot, as shown in FIG. 6A, and the optical axis of the objective lens 4 is set to 90 degrees relative to the insertion direction s. That is, the field of view moves to 90 degrees. At this time, as shown in FIG. 6C, illumination light is illuminated to the range of the field-of-view in the direction of 90 degrees from the illumination area 6c of the illumination port 6.

Accordingly, the optical axis of the objective lens 4 changes linearly from 0 to 90 degrees by pivoting of the imaging section 5, and the field of view is moved also linearly from 0 to 90 degrees. Simultaneously, the illumination light moves integrally so as to cover the range of the moving field-of-view. The directions of 0, 45, and 90 degrees shown in FIGS. 4A, 4B, 4C, 5A, 5B, 6A, 6B, and 6C are not particularly limited but are described as typical examples among 0 to 90 degrees. In the present embodiment, the imaging section is pivoted by a drive mechanism based on a rack and a pinion. However, the embodiment is not limited to this mechanism but the drive mechanism may be configured, for example, by using a wire and a pool or a minimum motor, etc.

Described next will be the illumination-light switching mechanism which selects/switches a partial illumination area depending on a moved field of view.

FIG. 7A shows a cross-sectional configuration of the illumination-light switching mechanism on the side of the insertion section, viewed from the side of A-A in FIG. 3. FIG. 8A shows a cross-sectional configuration of the illumination-light switching mechanism on the side of the universal cable, viewed from the side of B-B in FIG. 3. FIG. 8B shows a schematic configuration of the illumination-light switching mechanism viewed in an oblique direction from the B-B side.

The illumination-light switching mechanism of the present embodiment is configured mainly by the grip 11, the rotary ring 12, the cam 13, and a grip end 21, as shown in FIG. 3. The illumination-light switching mechanism is provided in the base-end side of the insertion section 2, integrally with the field-of-view switching mechanism described above. In the present embodiment, the illumination light switching mechanism is contained in the operation section 9 provided at a base end thereof.

In the illumination-light switching mechanism on the side of the rotary ring 12 (light outlet surface 15a) shown in FIG. 8A, the flat light outlet surface 15a made of a fiber end face is provided inside the cam 13, in a semicircular shape having a length of ¼ of the circumference. In a center part thereof, there are provided the grip 11 which supports the fixed pipe 11a, and the operation half-pipe 18 engaged to be movable back and forth.

Also as shown in FIG. 3, in the illumination-light switching mechanism (incident light-guide cap) on the side of the insertion section (light inlet surface 15b), the grip end 21 is screwed on the tip end of the operation section 9 by a screw so as to make contact with the rotary ring 12. In the incident light-guide cap shown in FIG. 7, the light guide fiber 15 which receives light flux from the light outlet surface 15a of the cam 13 is provided semi-circularly inside the grip tip end 21, and the flat light inlet surface 15b made of a fiber end face is provided. In a center part thereof, there are provided the grip 11 which supports the fixed pipe 11a, and the operation half-pipe 18 engaged to be movable back and forth.

Thus, the light outlet surface 15a which illuminates light flux of the illumination light introduced from an unillustrated light source in an arcuate shape, and the light inlet surface 15b having a semicircular shape which guides light to the illumination port 6 are movably opposed to each other, in the illumination light switching mechanism. In the configuration of the present embodiment, the light inlet surface 15b of the grip end 21 is fixed to the operation section 9. In accordance with rotation of the rotary ring 12, the light outlet surface 15a of the cam 13 rotates/moves, opposed to the light inlet surface 15b. At this time, there is no leakage of light to outside.

In this example, the light inlet surface 15b is a semi-circular arc longer than the light outlet surface 15a which has an arc of ¼ of the circumstance. Total light flux emitted from the light outlet surface 15a enters into a partial area of the light inlet surface 15b, and is guided to the illumination port 6. The illumination light is illuminated from the partial area (6a, 6b, and 6c) of the whole illumination port 6. An area ratio between the light outlet surface 15a and the light inlet surface 15b is set at any arbitrary time during designing.

With reference to FIGS. 9, 10A, 10B, 11A, 11B, 12A, and 12B, a description will be made of switching operation of the field of view and movement of the illumination area in the illumination light switching mechanism.

In the operation section 9, the illumination-light switching mechanism of the present embodiment is configured to be integral with the field-of-view switching mechanism described above. Therefore, the illumination area is moved, targeting only the field of view to be illuminated, in synchronism with switching operation of the field of view of the field-of-view switching mechanism by the operation section (rotary ring 12) 4.

Figure 9:
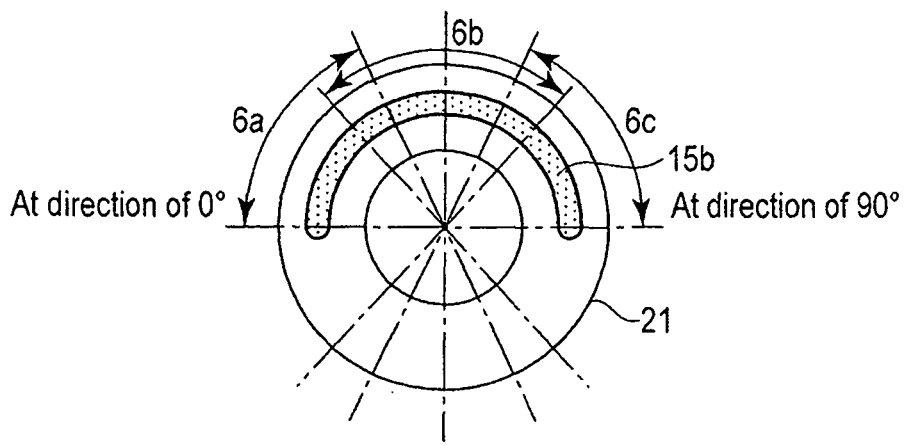
FIG. 9 shows an example configuration of a light inlet surface provided inside a grip end.
Figure 10A:
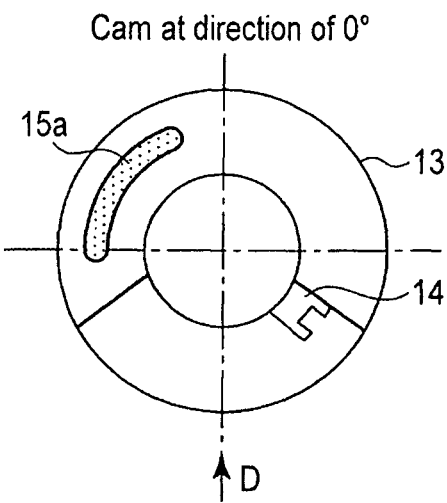
FIG. 10A shows a position of the light outlet surface where the field of view of the imaging section is directed in the direction of 0 degree.
Figure 10B:
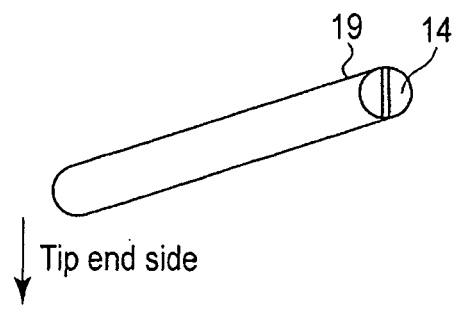
FIG. 10B shows a position of a cam pin in a guide hole corresponding to the position of a light outlet surface.
Figure 12A:
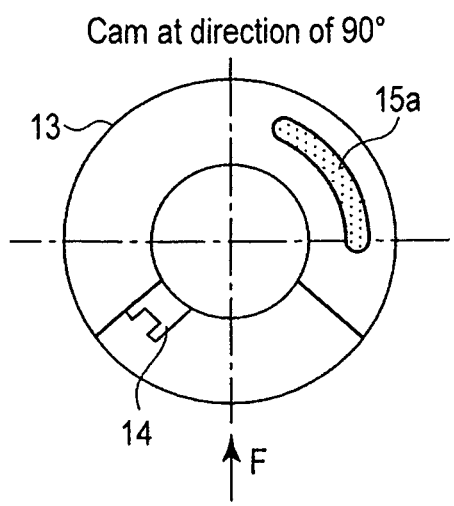
FIG. 12A shows a position of the light outlet surface where the field of view of the imaging section is directed in the direction of 90 degrees.
Figure 12B:
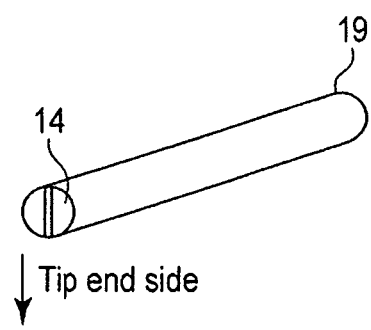
FIG. 12B shows a position of the cam pin in a guide hole corresponding to the position of the light outlet surface.

FIG. 9 shows an example configuration of the light inlet surface 15b provided inside the grip end 21. FIG. 10A shows a position of the light outlet surface 15a provided in the cam 13 where the field of view of the imaging section is in the direction of 0 degree. FIG. 10B shows a position of the cam pin 14 in the guide hole 19, which corresponds to the position of the light outlet surface 15a. FIG. 11A shows the position of the light outlet surface 15a provided in the cam 13 where the field of view of the imaging section is in the direction of 45 degrees. FIG. 11B shows a position of the cam pin 14 in the guide hole 19, which corresponds to the position of the light outlet surface 15a. FIG. 12A shows a position of the light outlet surface 15a provided in the cam 13 where the field of view of the imaging section is in the direction of 90 degrees. FIG. 12B shows a position of the cam pin 14 in the guide hole 19, which corresponds to the position of the light outlet surface 15a.

If the optical axis of the objective lens 4 of the imaging section 5 is coaxial with the insertion direction s, the light outlet surface 15a exists at the left end (at the direction of 0 degree) of the movable range, as shown in FIG. 10A. The cam pin 14 exists in the most rear end side of the inclined guide hole 19. At these positions, the light flux introduced from the light source enters into the partial illuminated field 6a of the light inlet surface 15b shown in FIG. 9. As shown in FIGS. 4C, 5B, and 6C, illumination light is illuminated from a partial area of the illumination port 6 in a manner that the center of the partial illumination area 6a ranges so as to cover the field of view range from 0 to 90 degrees.

When the operator rotates the rotary ring 12, the light outlet surface 15a exists at the center (at the direction of 45 degrees) of the movable range, for example, as shown in FIG. 11A. The cam pin 14 exists in the center of the guide hole 19. In these positions, the light flux introduced from the light source enters into the partial illumination area 6a of the light inlet surface 15b shown in FIG. 9. As shown in FIG. 5B, the illumination light is illuminated from the illumination window in a manner that the center of the partial illumination area 6b at 45 degrees ranges so as to cover the range of the field of view.

Further, when the operator rotates the rotary ring 12, the light outlet surface 15a exists at the right end (at the direction of 90 degrees) of the movable range, for example, as shown in FIG. 12A. The cam pin 14 exists in the most front end side of the onliquely inclined guide hole 19. In these positions, the light flux introduced from the light source enters into the partial illumination area 6c of the light inlet surface 15b shown in FIG. 9. As shown in FIG. 6C, the illumination light is illuminated from the illumination window in a manner that the center of the partial illumination area 6c at 90 degrees ranges so as to cover the range of the field of view.

In the present embodiment, the light outlet surface 15a exemplifies an arc having a length of ¼ of the circumference for the cam 13 having a disc shape. The arc length is not limited to this length but may be appropriately changed. The arc length is proportional to the area size of the illumination window from which illumination light is illuminated.

As described above, the present embodiment provides the illumination-light switching mechanism which moves a partial illumination area corresponding to the field of view, in synchronism with pivoting of the imaging section by the field-of-view switching mechanism formed integrally. That is, the illumination section has an illumination range of illumination light which covers the whole field of view and moves within the illumination range in synchronism with pivoting of the imaging section. Accordingly, the illumination section can illuminate a partial illumination area with illumination light so as to comply with a current field of view.

Therefore, according to the present embodiment, only the current field of view of the field-of-view range is illuminated. In this manner, wasteful consumption of energy is reduced, and an amount of excessive illumination light is suppressed. A temperature rise at the tip end of the endoscope is suppressed, and reduction of size of the insertion section is realized.

[First Modification of First Embodiment]

A modification of the first embodiment will now be described.

In the first embodiment described above, the illumination area of the light inlet surface 15b is selected by rotating the cam. However, the present modification is configured to provide an optical deflection member and a reflective member in combination, such as a pivotal prism and a mirror, between the light outlet surface 15a and the light inlet surface 15b in the operation section 9. Based on the angle of the field of view of the imaging section 5, a mirror positioned in correspondence with the illumination area of the light inlet surface 15b is selected to guide illumination light by the optical deflection member.

According to the present modification, operation and effects equivalent to the first embodiment can be achieved.

[Second Modification of First Embodiment]

Another modification of the first embodiment will now be described.

The first modification described above is configured to combine an optical deflection member and a reflective member, such as a prism and a mirror. However, the present modification employs a scanning drive mirror (scanning mirror) mounted on a bar code reader. The scanning mirror is pivotally supported on a mirror back surface, and moves the scanning mirror like a pendulum by providing an electromagnet close to the magnet supported in a side opposite to the mirror and by reversing polarities at a predetermined timing. The light outlet surface 15a and the light inlet surface 15b are positioned at an angle maintained between each other. The scanning mirror is provided therebetween. Illumination light (light flux) emitted from the light outlet surface 15a is configured to be reflected to enter into the light inlet surface 15b. Further, blinking light is used as illumination light, and a lighting timing and a scanning timing of the scanning mirror are matched with each other. The illumination light can be made enter into an arbitrary area of the light inlet surface 15b.

According to the present modification, operation and effects equivalent to the first embodiment can be achieved.

Second Embodiment

Next, an illumination-light switching mechanism according to the second embodiment will be described with reference to FIGS. 13A, 13B, and 13C.

A field-of-view switching mechanism of the present embodiment is configured to divisionally shield light flux introduced from a light source by using a liquid crystal shutter, and to illuminate only illumination light which illuminates a current field of view to image by an imaging section, from an illumination window.

FIG. 13A conceptually shows an example configuration of the illumination-light switching mechanism provided at a tip end of the insertion section of a rigid endoscope. FIG. 13B shows a light inlet surface on the side of the insertion section. FIG. 13C shows a light outlet surface which includes a liquid-crystal shutter. The field-of-view switching mechanism which pivots the imaging section to move the field of view is equivalent to that of the first embodiment described above, and will be denoted at the common reference signs. Descriptions thereof will be therefore omitted herefrom.

The illumination-light switching mechanism of the present embodiment is configured by: a liquid-crystal shutter section 31 which is connected to a light guide fiber 15 and comprises a liquid-crystal shutter to allow illumination light to selectively penetrate (or shield) to be guided to a plurality of illumination windows 34 (34a, 34b, 34c, 34,d, 34e, and 34f); and a divisional light-guide fiber section 32 which is connected to the liquid-crystal shutter section 31 and guides the illumination light to each of the illumination windows 34. The illumination-light switching mechanism may be provided in the operation section 9 or may be provided at a tip end part of the endoscope as long as no thermal problem occurs.

From the divisional light-guide fiber section 32 to the illumination windows 34a, 34b, 34c, 34d, 34e, and 34f, illumination light is guided through light guide fibers 33a, 33b, 33d, 33e, and 33f, respectively. The illumination window in the first embodiment described above has an illumination range of illumination light which covers a whole field of view with a window. However, the present embodiment is an example configuration of individually dividing illumination windows. Of course, the illumination window of the first embodiment may be applied in place of the illumination windows of the present embodiment.

In FIG. 13B, a light inlet surface 15b on the side of a tip end is provided, divided into partial light inlet surfaces 35a, 35b, 35c, 35d, 35e, and 35f respectively corresponding to the light guide fibers 33a, 33b, 33d, 33e, and 33f. In FIG. 13C, liquid-crystal shutter surfaces 36a, 36b, 36c, and 36d divided into, for example, four areas are provided in the light outlet surface 15a on the side of the operation section 9. These light inlet surface 15b and light outlet surface 15a are jointed to be opposed so as not to leak light.

A sensor is provided on a rotary ring 12 which rotates the imaging section 5, to obtain an angle of a field of view of the imaging section 5 (an optical axis angle of an objective lens 4). Angle information (sensor signal) of the sensor is outputted to an unillustrated liquid-crystal-shutter drive mechanism.

In the illumination-light switching mechanism configured as described above, for example, when the imaging section 5 has a field of view in the direction of 0 degree, the illumination light penetrates the liquid-crystal shutter surfaces 36a and 36b, and the other illumination light is shielded by the liquid-crystal shutter surfaces 36c and 36d. Similarly, when the imaging section 5 has a field of view in the direction of 45 degrees, the illumination light penetrates the liquid-crystal shutter surfaces 36b and 36c, and the other illumination light is shielded by the liquid-crystal shutter surfaces 36a and 36d. Further, when the imaging section 5 has a field of view in the direction of 90 degrees, the illumination light penetrates the liquid-crystal shutter surfaces 36c and 36d, and the other illumination light is shielded by the liquid-crystal shutter surfaces 36a and 36b.

As described above, according to the present embodiment, only the current field of view within the range of the field-of-view is illuminated as in the first embodiment described previously. In this manner, an excessive amount of illumination light is suppressed, and a temperature rise at the tip end part of the endoscope is also suppressed. In addition, reduction of size of the insertion section is achieved. Since there is no mechanical component, the embodiment can be practiced at low cost. Since electric drive control is available, operation is easy.

Third Embodiment

Next, an illumination-light switching mechanism according to the third embodiment will be described with reference to FIGS. 14, 15A, and 15B. A field-of-view switching mechanism of the present embodiment is configured to allow light flux introduced from a light source to divisionally penetrate by using cutout windows, and to illuminate only illumination light which illuminates a current field of view of an imaging section from an illumination window.

FIG. 14 shows an exterior configuration of the illumination-light switching mechanism provided at a tip end of the insertion section of a rigid endoscope. FIG. 15A shows a light inlet surface on the side of the insertion section. FIG. 15B shows a light outlet surface which includes a mechanical shutter plate. The field-of-view switching mechanism which pivots an imaging section to move a field of view is equivalent to that of the first embodiment described above, and will be denoted at the common reference signs. Descriptions thereof will be therefore omitted herefrom.

The field-of-view switching mechanism of the present embodiment is an example configuration which uses a mechanical shutter in place of a liquid-crystal shutter. In the configuration, light flux introduced from a light source is allowed to partially penetrate, and only illumination light which illuminates the current field of view of the imaging section is illuminated from an illumination window.

As shown in FIG. 14, illumination light is guided by: a shutter plate 42 comprising a cutout which allows (or shield) illumination light to selectively penetrate to be guided to a plurality of illumination windows 41 (41a, 41b, 41c, and 41d); and unillustrated divisional light guide fibers which are provided close to the shutter plate 42 and guide the illumination light to the illumination windows 41, respectively. The shutter plate 42 is rotatably pivoted at the center, and can be rotated in any rotation direction by an unillustrated drive unit not shown.

Also in the present embodiment, based on the angle of the field of view of the imaging section 5, i.e., based on the angle of the optical axis of the objective lens 4, the shutter plate 42 is rotated, as in the first embodiment described above, to align a cutout 44 with an area of a light inlet surface corresponding to an illumination area of the illumination light. In this manner, the illumination light is allowed to penetrate and illuminate an object to observe from the illumination windows 41.

The present embodiment describes an example in which illumination light is allowed to penetrate a semi-circular light inlet surface 15b by using the shutter plate 42 including a cutout 44 formed with a length of ¼ of the circumference.

As shown in FIG. 15A, for example, when the imaging section 5 has a field of view in the direction of 0 degree, the cutout 44 in the shutter plate 42 is positioned at a left end 44a, to allow the illumination light to penetrate. The other illumination light is shielded by the shutter plate 42. The illumination light is illuminated only from the illumination windows 41a and 41b shown in FIG. 14. Similarly, when the imaging section 5 has a field of view in the direction of 45 degrees, the cutout 44 is positioned at a center 44b, to allow the illumination light to penetrate. The illumination light is illuminated only from the illumination windows 41b and 41c. Further, when the imaging section 5 has a field of view in the direction of 90 degrees, the cutout 44 is positioned in the right end 44*c*, to allow the illumination light to penetrate. The illumination light is illuminated only from the illumination windows 41*c* and 41*d*.

As described above, according to the present embodiment, only the current field of view within the range of the field-of-view to image is illuminated as in the first embodiment described previously. In this manner, an excessive amount of illumination light is suppressed, and a temperature rise at the tip end part of the endoscope is also suppressed. In addition, reduction of size of the insertion section is achieved.

The above embodiments have been described with reference to a tip end provided in a rigid endoscope. However, the embodiments are also applicable to a tip end provided at an insertion section in an elastic endoscope in the same manner as described above, and equivalent operation and effects can be achieved.

Also the above embodiments have been described with reference to an example in which the field of view moves throughout a range of 0 to 90 degrees. Of course, these angles are not limited but a substantial object of the embodiments is to provide a system which comprises an area of an illumination port covering a whole range of the field of view, where the field of view is movable, and switches partial illumination areas of the illumination port so as to move integrally together with the current field of view. Insofar as the field of view exceeds 0 or 90 degrees in either direction (0 or less or 90 or more), the illumination light is moved to an equivalently excessive angle.

According to the embodiments of the invention, there is provided a medical devicemedical device mounting an imaging apparatus which moves a field of view, and comprising an illumination apparatus which selectively illuminates a range of a field of view, wherein energy consumed by illumination is suppressed, and reduction of size of an insertion section is achieved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical device comprising:
an observation section that observes a field of view;
a field-of-view switching mechanism that moves an area of the field of view observed by the observation section within a predetermined range by pivoting the observation section in accordance with movement operation by an operation portion;
an illumination section that illuminates illumination light guided from outside of the operation portion, in a predetermined direction including the range through an illumination port;
an illumination-light switching mechanism comprising a light outlet surface that emits the illumination light guided from the outside, and a light inlet surface that is opposed to the light outlet surface and allows the illumination light emitted from the light outlet surface and guided to the illumination port to enter therethrough, wherein the light outlet surface moves in relation to the light inlet surface, in accordance with the movement operation by the operating portion, and the illumination-light switching mechanism is provided inside the operation portion on a light guide path which guides the illumination light from the outside from the light outlet surface to the light inlet surface to selectively guide the illumination light to a part of the illumination port in accordance with movement operation of pivoting the operation portion; and
a synchronous section provided inside the operation portion and comprising a mechanism that makes the illumination port that emits the illumination light to the field of view observed by the observation section selectively emit the illumination light, in synchronism with operation of the field-of-view switching mechanism that pivots the observation section by the movement operation by the operation portion,
the synchronous section performing switching to make the illumination-light switching mechanism operate so as to selectively emit the illumination light to the light inlet surface, in synchronism with the operation of the field-of-view switching mechanism of moving the observation section to the range of the field of view, by pivoting the operation portion.

2. The medical device of claim 1, wherein
the field-of-view switching mechanism moves the field of view by pivoting the observation section in accordance with movement operation of pivoting the operation portion.

3. A medical device comprising:
an observation section that observes a field of view;
a field-of-view switching mechanism that moves an area of the field of view observed by the observation section within a predetermined range by pivoting the observation section in accordance with movement operation by an operation portion;
an illumination section that illuminates illumination light guided from outside of the operation portion, in a predetermined direction including the range through an illumination port;
an illumination-light switching mechanism comprising a light outlet surface that is integral with the operation portion, and emits the illumination light guided from the outside, and a light inlet surface that has a larger area than the light outlet surface, is opposed to the light outlet surface, and allows the illumination light emitted from the light outlet surface and guided to the illumination port to enter therethrough, wherein the light outlet surface relatively pivots in relation to the light inlet surface, in accordance with the movement operation by the operation portion, and the illumination-light switching mechanism is provided inside the operation portion on a light guide path which guides the illumination light from the outside from the light outlet surface to the light inlet surface to selectively guide the illumination light to a part of the illumination port in accordance with movement operation of pivoting the operation portion; and
a synchronous section provided inside the operation portion and comprising a mechanism that makes the illumination port that emits the illumination light to the field of view observed by the observation section selectively emit the illumination light, in synchronism with operation of the field-of-view switching mechanism that pivots the observation section by the movement operation by the operation portion,
the synchronous section performing switching to make the illumination-light switching mechanism operate so as to selectively emit the illumination light to the light inlet surface, in synchronism with the operation of the fieldof-view switching mechanism of moving the observation section to the range of the field of view, by pivoting the operation portion.

4. The medical device of claim 1, wherein
the observation section is provided at a tip end of an insertion section of an endoscope, and
the field-of-view switching mechanism and the illumination-light switching mechanism are provided integrally to operate in synchronism with each other by the movement operation through the synchronous section in the operation portion provided in a base-end side of the insertion section.

5. The medical device of claim 1, wherein
the field-of-view switching mechanism comprises,
the operation portion,
a swing section that swings the observation section, which is pivotally supported, within a desired angular range, and
an engagement pin that is provided on an elongate axial member jointed to the swing section and pushes and pulls the swing section in an axial direction, and a cam member that comprises a guide hole in which the engagement pin is engaged and which extends in a direction oblique to the axial direction, that pivots the guide hole in a direction perpendicular to the axial direction, and is fixed integrally to the operation portion, and
when the operation portion is pivoted, the guide hole is rotated by the cam member and reciprocally moves the engagement pin in the axial direction in the guide hole, thereby swinging the swing section and to accordingly pivot the observation section to a desired angle.

6. The medical device of claim 3, wherein
the field-of-view switching mechanism comprises,
the operation portion
a swing section that swings the observation section, which is pivotally supported, within a desired angular range, and
an engagement pin that is provided on an elongate axial member jointed to the swing section and pushes and pulls the swing section in an axial direction, and a cam member that comprises a guide hole in which the engagement pin is engaged and which extends in a direction oblique to the axial direction, that pivots the guide hole in a direction perpendicular to the axial direction, and is fixed integrally to the operation portion, and
when the operation portion is pivoted, the guide hole is rotated by the cam member and reciprocally moves the engagement pin in the axial direction in the guide hole, thereby swinging the swing section and to accordingly pivot the observation section to a desired angle.

7. The medical device of claim 1, wherein the illumination-light switching mechanism comprises:
an emitting light-guide cap that is integrally connected to the operation portion and is provided with the light outlet surface; and
an incident light-guide cap that is adjacent to the light-guide emission cap, is provided to be fixed to the operation portion, and is provided with the light inlet surface opposed to the light outlet surface, wherein
the illumination light is illuminated from a part of the illumination window targeting the moved field of view, by changing an opposed position relative to the light outlet surface where the light inlet surface is at a fixed position, in accordance with operation of the operation portion.

8. The medical device of claim 3, wherein the illumination-light switching mechanism comprises:
an emitting light-guide cap that is integrally connected to the operation portion and is provided with the light outlet surface;
an incident light-guide cap that is adjacent to the emitting light-guide cap, is provided to be fixed to the operation portion, and is provided with the light inlet surface opposed to the light outlet surface, wherein
the illumination light is illuminated from a part of the illumination window targeting the moved field of view, by changing an opposed position of the light inlet surface relative to the light outlet surface existing at a fixed position, in accordance with operation of the operation portion.

9. A medical device comprising:
an observation section that observes a field of view;
a field-of-view switching mechanism that moves an area of the field of view observed by the observation section within a predetermined range by pivoting the observation section in accordance with movement operation by an operation portion;
an illumination section that illuminates illumination light guided from outside of the operation portion, in a predetermined direction including the range through an illumination port;
an illumination-light switching mechanism comprising a light outlet surface that emits the illumination light guided from the outside, a light inlet surface that is opposed, throughout a whole surface thereof, to the light outlet surface and allows the illumination light emitted from the light outlet surface and guided to the illumination port to enter therethrough, and a shutter section that is provided between the light inlet surface and the light outlet surface, and allows the illumination light emitted from the light outlet surface to partially penetrate, the illumination-light switching mechanism being provided inside the operation portion on a light guide path which guides the illumination light from the outside from the light outlet surface to the light inlet surface to selectively guide the illumination light to a part of the illumination port in accordance with movement operation of pivoting the operation portion; and
a synchronous section provided inside the operation portion and comprising a mechanism that performs switching so as to make the shutter section to allow the illumination light emitted from the light outlet surface to penetrate in a manner that the illumination-light switching mechanism selectively guides the illumination light emitted from the light outlet surface to the light inlet surface, in synchronism with operation of the field-of-view switching mechanism that pivots the observation section by the movement operation by the operation portion,
the synchronous section performing switching to make the illumination-light switching mechanism operate so as to selectively emit the illumination light to the light inlet surface, in synchronism with the operation of the field-of-view switching mechanism of moving the observation section to the range of the field of view, by pivoting the operation portion.

10. The medical device of claim 1, wherein the observation section comprises:
an imaging unit that comprises an imaging sensor and generates a video signal; and
an optical system configured by an objective lens that forms an optical image of the object to observe, and a light guide section that guides the optical image to the imaging unit, wherein the imaging unit and the optical system are configured to be mechanically separate from each other, and only the optical system is pivoted by the field-of-view switching mechanism, to guide the optical image formed by the optical system to the imaging unit.

11. The medical device of claim 3, wherein the observation section comprises:
an imaging unit that comprises an imaging sensor and generates a video signal; and
an optical system configured by an objective lens that forms an optical image of the object to observe, and a light guide section that guides the optical image to the imaging unit, wherein
the imaging unit and the optical system are configured to be mechanically separate from each other, and only the optical system is pivoted by the field-of-view switching mechanism, to guide the optical image formed by the optical system to the imaging unit.

12. The medical device of claim 9, wherein the observation section comprises:
an imaging unit that comprises an imaging sensor and generates a video signal; and
an optical system configured by an objective lens that forms an optical image of the object to observe, and a light guide section that guides the optical image to the imaging unit, wherein
the imaging unit and the optical system are configured to be mechanically separate from each other, and only the optical system is pivoted by the field-of-view switching mechanism, to guide the optical image formed by the optical system to the imaging unit.

13. The medical device of claim 1, wherein the field-of-view switching mechanism is a rotation mechanism in which a gear section is formed in the observation section and is engaged with a moving rack section.

14. The medical device of claim 3, wherein the field-of-view switching mechanism is a rotation mechanism in which a gear section is formed in the observation section and is engaged with a moving rack section.

15. The medical device of claim 9, wherein the field-of-view switching mechanism is a rotation mechanism in which a gear section is formed in the observation section and is engaged with in a moving rack section.

16. The medical device of claim 10, further comprising a shielding section that selectively shields light, with respect to a plurality of light guide areas into which the light guide section is divided.

17. The medical device of claim 10, wherein
the light guide section comprises an incident cap that supports all emission directions at an incident end, an emission direction controller comprises an emission cap that emits the illumination light in a desired one of all the emission directions, and the incident cap and the emission cap are combined in a manner that ends of both the caps are opposed to each other.

18. The medical device of claim 17, wherein
the emission direction controller is moved or rotated in relation to the emission cap and the incidence cap.

* * * * *